(12) United States Patent
Takata et al.

(10) Patent No.: US 8,207,357 B2
(45) Date of Patent: Jun. 26, 2012

(54) ROTAXANE COMPOUND AND ANTITUMOR AGENT

(75) Inventors: Toshikazu Takata, Tokyo (JP); Yasuhito Koyama, Tokyo (JP); Kazuko Nakazono, Tokyo (JP); Toshihide Hasegawa, Tokyo (JP); Young-Gi Lee, Tokyo (JP); Nobufumi Ono, Fukuoka (JP); Kazuto Nishio, Osakasayama (JP); Yoshihiko Fujita, Osakasayama (JP)

(73) Assignees: Wan Station Co., Ltd., Tokyo (JP); Tokyo Institute of Technology, Tokyo (JP); Fukuoka University, Fukuoka-shi (JP); Kinki University, Higashiosaka-shi (JP)

( * ) Notice: Subject to any disclaimer, the term of this patent is extended or adjusted under 35 U.S.C. 154(b) by 0 days.

(21) Appl. No.: 13/125,394

(22) PCT Filed: Oct. 21, 2009

(86) PCT No.: PCT/JP2009/005503
§ 371 (c)(1),
(2), (4) Date: Jun. 21, 2011

(87) PCT Pub. No.: WO2010/047094
PCT Pub. Date: Apr. 29, 2010

(65) Prior Publication Data
US 2011/0237807 A1 Sep. 29, 2011

(30) Foreign Application Priority Data
Oct. 21, 2008 (JP) .................................. 2008-270424

(51) Int. Cl.
*C07D 323/00* (2006.01)
(52) U.S. Cl. ...................................................... 549/348
(58) Field of Classification Search .................. None
See application file for complete search history.

(56) References Cited

FOREIGN PATENT DOCUMENTS

| JP | 3741706 B2 | 2/2006 |
| JP | 3887008 B1 | 2/2007 |
| JP | 2009-067699 A | 4/2009 |
| WO | 2008/044704 A1 | 4/2008 |

OTHER PUBLICATIONS

Arteaga et al., Clinical Cancer Research, vol. 9, 2003, 1579-1589.*
Arbiser, The Journal of Clinical Investigation, 117, 10, 2762-2765.*
Madhusudan et al., Clinical Biochemistry, 2004, 37, 618-635.*
Ono, caplus an 2007:214595.*
Kihara N. et al. "Direct preparation of rotaxane from aminoalcohol: selective O-acylation of aminoalcohol in the presence of trifluoromethanesulfonic acid and crown ether," Chemistry Letters, 2001, vol. 6, pp. 592-593, cited in ISR (not enclosed).
"Cho Bunshi Kagobutsu (Rotaxane) no Gan Saibo Zoshoku ni Taisuru Eikyo," Heisei 19 Nendo Dai 24 Kai Nippon Yakugakkai Kyushu Shibu Taikai Koen Yoshishu, Nov. 15, 2007, p. 107, cited in ISR (not enclosed).
"Kogan Kassei o Motsu Rotaxane no Gosei," 89th Annual Meeting of Chemical Society of Japan in Springs Koen Yokoshu II, Mar. 13, 2009, 1 E2-12, p. 875, cited in ISR (not enclosed).
International Search Report of PCT/JP2009/005503, mailing date Nov. 24, 2009.

* cited by examiner

*Primary Examiner* — Sun Jae Loewe
(74) *Attorney, Agent, or Firm* — Westerman, Hattori, Daniels & Adrian, LLP

(57) ABSTRACT

An antitumor agent which is not easily excreted from tumor cells and is suitable for a topical treatment. Specifically disclosed is a rotaxane compound with contains a compound represented by chemical formula 1 as the base structure. (In chemical formula 1, $m \geq 2$, $n \geq 3$, and X represents an anionic molecule or an anionic atom.

12 Claims, 2 Drawing Sheets

ROTAXANE COMPOUND AND ANTITUMOR AGENT

TECHNICAL FIELD

The present invention relates to a rotaxane compound that can be used as an antitumor agent and an antitumor agent containing the compound as an active ingredient.

BACKGROUND ART

In many antitumor agents, their antitumor activities are shown only after the agent is absorbed in tumor cells. Therefore, it has been thought that drugs having low molecular weights and stable structures are effective as antitumor agents in order to make it easy for the drugs to be taken in through receptors of tumor cells.

However, the antitumor agent that can be easily absorbed in tumor cells through the receptors is also easily excreted from the cells conversely. Accordingly, there has been a problem that the antitumor agent cannot stay in tumor cells for a sufficient length of time to show its antitumor activity. In addition, such an antitumor agent that is easily absorbed through the receptors is easily taken in normal cells as well as in tumor cells and, therefore, is difficult to be used for topical treatment and causes a problem of the side effect due to injury of the normal cells.

On the other hand, high molecular compounds, such as a catenane compound in which two ring-shaped molecules are bound to each other like a chain with no covalent bond, and a rotaxane compound having a structure in which a linear molecule stays through a ring-shaped molecule with no covalent bond, have large molecular weights and have high degrees of freedom in positional relationship between two structural units. Therefore, it is thought that the high molecular compounds that have been once taken in cells are not easily excreted. Accordingly, these high molecular compounds are promising candidates for antitumor agents. Antitumor agents utilizing these high molecular compounds are disclosed in Patent Document 1 (catenane compound) and in Patent Document 2 (rotaxane compound) as below.

PATENT DOCUMENTS

Patent Document 1: JP 3741706B.
Patent Document 2: JP 3887008B.

SUMMARY OF INVENTION

The rotaxane compound disclosed in Patent Document 2 has a structure shown by the following Chemical Formula 2.

[Formula 2]

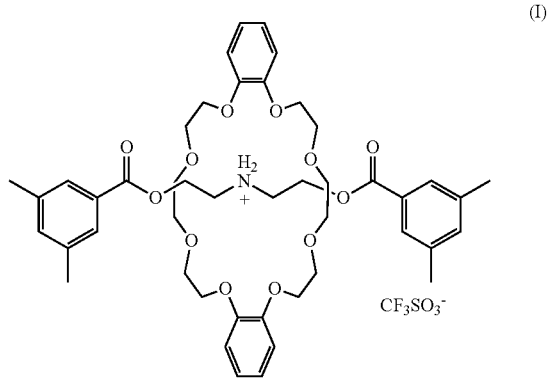

The compound shown by the above Chemical Formula 2 has been recognized to have a growth-inhibition effect on tumor cells as described in the document. It is an object of the present invention to provide a rotaxane compound having a higher molecular weight than that of the above-mentioned compound and having an antitumor activity comparable to or higher than that of the compound.

In the light of the above-mentioned object, the rotaxane compound according to the present invention includes a compound represented by the following Chemical Formula 3 as a basic structure (in Chemical Formula 3, $m \geq 2$, $n \geq 3$, and X represents an anionic molecule or an anionic atom).

[Formula 3]

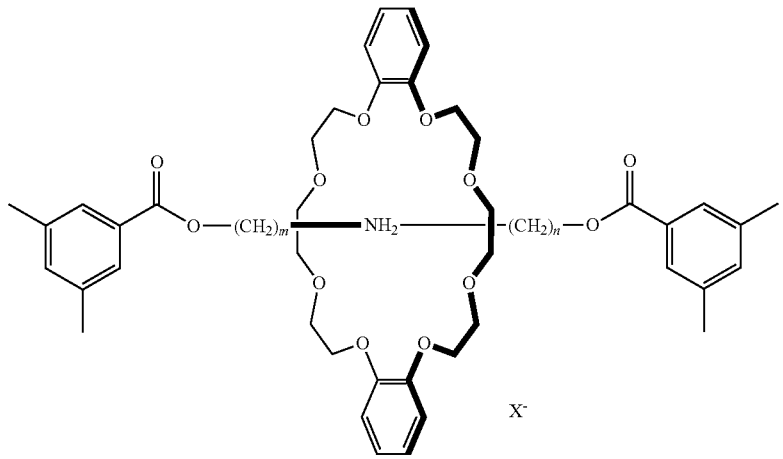

Herein, a compound including the above-described compound as a basic structure refers to not only the above-mentioned compound itself but also a compound in which an appropriate substituent is added to the above-mentioned compound. That is, in the present invention, as long as the above-mentioned compound is included as the basic structure, a functional group may be included in the ring-shaped portion. The functional group is not particularly limited as long as it can be structurally introduced, and specific examples thereof include a mercaptomethyl group, a mercapto group, an aminomethyl group, an amino group, a hydroxyl group, a hydroxymethyl group, a carboxyl group, a carboxymethyl group, a halogen group, an ether group, a thioether group, a carbamate group, an amide group, a peptide group, a vinyl group, an allyl group, an ethynyl group, an aldehyde group, an acrylate group, and a methacrylate group. In addition, the number of the functional groups introduced per molecule is not particularly limited as long as it is structurally acceptable.

The anionic molecule or the anionic atom represented by "X" is also not particularly limited, and specific examples thereof include a perchlorate ion, a trifluoromethanesulfonate ion, a hexafluorophosphate ion, a trifluoroacetate ion, and a tetrafluoroborate ion.

Among the rotaxane compounds according to the present invention, a compound having the lowest molecular weight is represented by the following Chemical Formula 4, wherein m=2, and n=3.

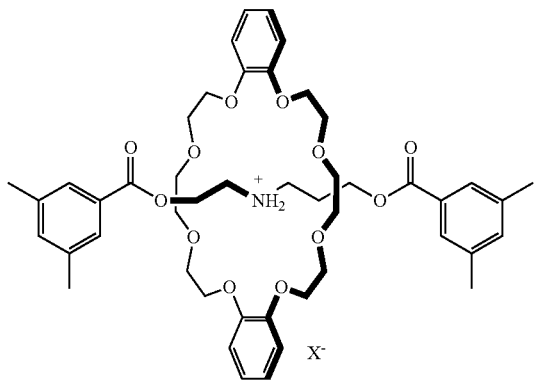

[Formula 4]

The rotaxane compound shown by Chemical Formula 4 is a compound formally called [2][(3,5-dimethylphenylcarboxyethyl)(3,5-dimethylphenylcarboxypropyl) ammonium-rotaxa-[2,5,8,11,13,16,19,22-octaoxa-1,12(1,2)-dibenzena-cyclodocosaphane]] trifluoromethanesulfonate, and has a molecular weight of 982.

Furthermore, in the rotaxane compound according to the present invention, it is preferable that $m \leq 5$ and $n \leq 5$. In this case, there are nine possible combinations of m and n: that is, in addition to (2,3) shown in Chemical Formula 4, (2,4), (2,5), (3,3), (3,4), (3,5), (4,4), (4,5), and (5,5). Among these rotaxane compounds, a compound having the highest molecular weight is represented by the following Chemical Formula 5, wherein m=n=5.

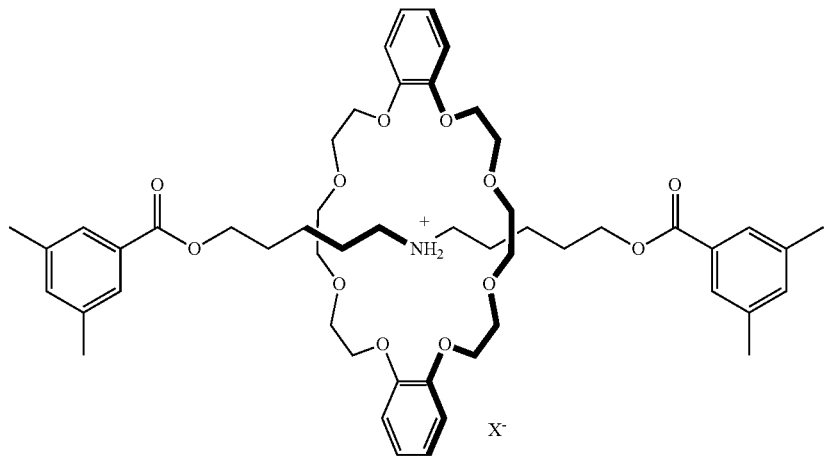

[Formula 5]

The rotaxane compound shown by this Chemical Formula 5 is a compound formally called [2][bis(3,5-dimethylphenyl-carboxypentyl)ammonium-rotaxa-[2,5,8,11,13,16,19,22-octaoxa-1,12(1,2)-dibenzenacyclodocosaphane]]trifluoromethanesulfonate and has a molecular weight of 1052.

Each of these rotaxane compounds is composed of two components: a rod-shaped component, to both ends of which relatively large molecules are bound, and a ring-shaped component (crown ether) into which the rod-shaped component is inserted. Since the rod-shaped component is threaded through the ring-shaped component, the ring-shaped component can move using the rod-shaped component as an axis. However, since the relatively large molecules are bound to both ends of the rod-shaped component, these molecules serve as stoppers to prevent the ring-shaped component from disengagement from the rod-shaped component.

Thus, though the rotaxane compound has a structure in which the rod-shaped component and the ring-shaped component are linked to each other, the rod-shaped component and the ring-shaped component are not bound by a covalent bond. Therefore, the molecule easily changes its shape to make it relatively difficult for the molecule to be taken in through a receptor, but tumor cells are prevented from growing when the rotaxane compound is once introduced into tumor cells. That is, the rotaxane compound according to the present invention acts as an active ingredient of an antitumor agent.

Thus, according to the present invention, it is possible to provide an antitumor agent that is hardly excreted from tumor cells and is suitable for topical treatment.

DESCRIPTION OF EMBODIMENTS (1) TRO-A0014

Figure 1:
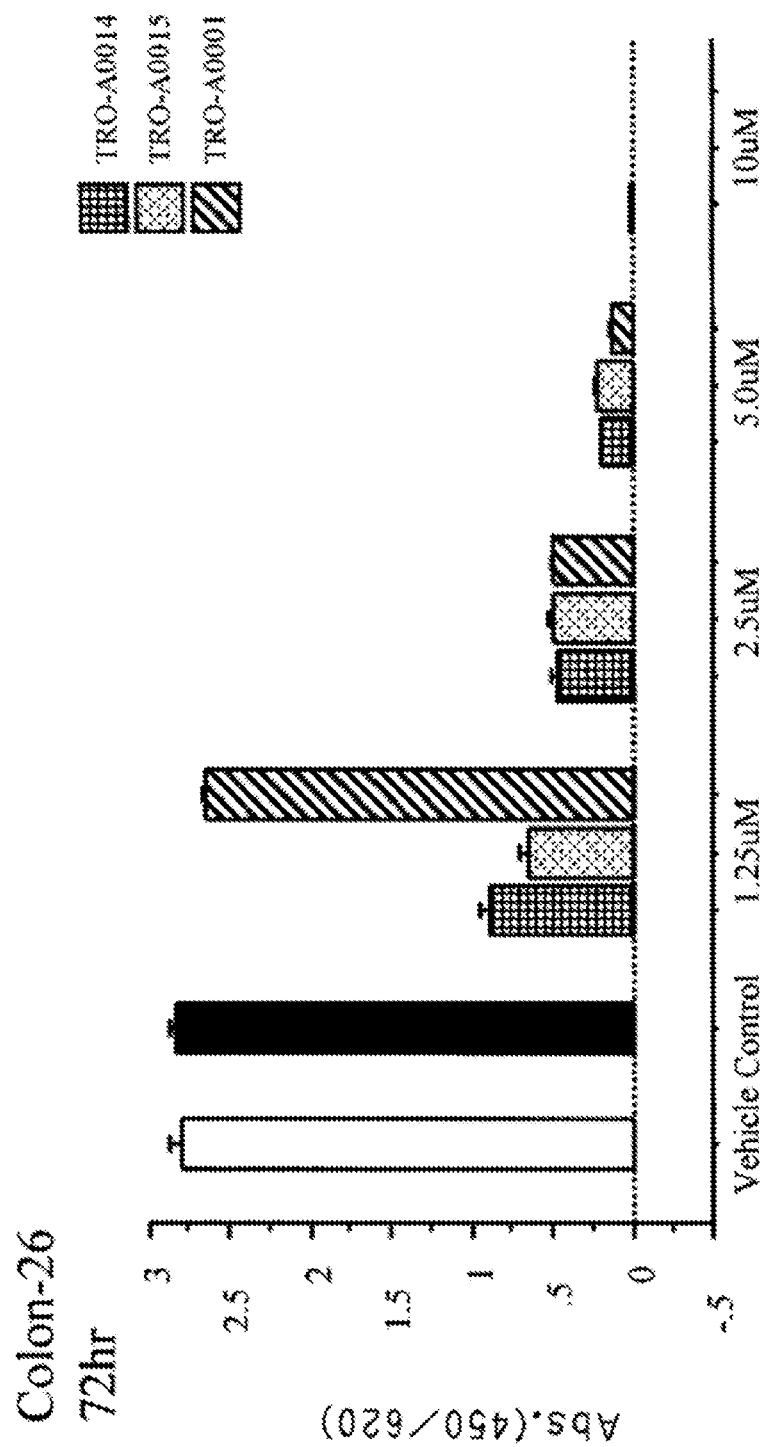
FIG. 1 A graph showing experimental results of antitumor activities of TRO-A0014 and TRO-A0015.

Among the rotaxane compounds according to the present invention, a compound in which m=2 and n=3 is referred to as "TRO-A0014". This TRO-A0014 was synthesized by a reaction shown by the following Chemical Formula 6.

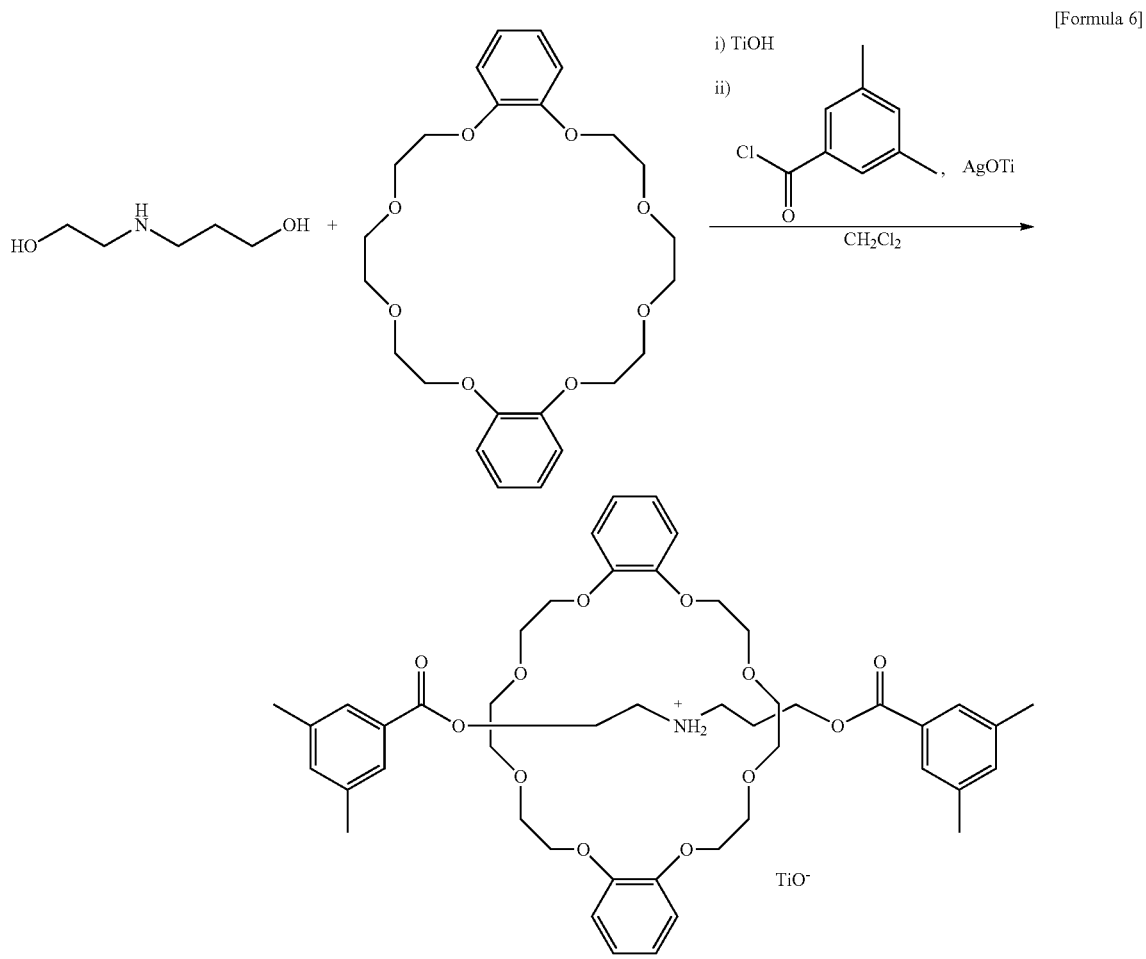

[Formula 6]

Specifically, 3-(2-hydroxyethylamino)propan-1-ol (200 mg, 1.68 mmol), dibenzo-24-crown-8-ether (753 mg, 1.68 mmol), and trifluoromethanesulfonic acid (148 mL, 1.68 mmol) were placed in a two-necked eggplant-shaped flask, followed by replacement with argon and then dissolved in $CH_2Cl_2$ (1 mL). The resulting solution was cooled to 0° C. and was stirred. Then, 3,5-dimethylbenzoyl chloride (566 mg, 3.36 mmol), having been replaced with argon and dissolution in $CH_2Cl_2$ (2.4 mL), was added thereto. Furthermore, after addition of silver trifluoromethanesulfonate (863 mg, 3.36 mmol), the temperature of the resulting mixture was gradually increased from 0° C. to room temperature, and the mixture was successively stirred at room temperature for 24 hours. After confirmation of TLC ($CHCl_3$/MeOH=10/1), saturated aqueous $Na_2CO_3$ was added to quench the reaction. Organic materials were extracted from the reaction mixture with $CHCl_3$, dried over $MgSO_4$, and subjected to filtration. The solvent was distilled away under reduced pressure. The obtained crude product was applied to silica gel column chromatography (eluent: $CHCl_3$/MeOH=1/0 to 10/1) and then to recycling HPLC (eluent: $CHCl_3$) for separation and purification to obtain a target compound.

The target compound was white-foamed solid, and the amount was 157 mg and the yield was 10%. The $^1$H NMR spectrum (400 MHz, $CDCl_3$, 298 K) of the obtained target compound was as follows, and it was confirmed that the obtained compound was the compound on the right side of the above-mentioned Chemical Formula 6:

That is, δ 7.65 (s, 2H), 7.52 (s, 2H), 7.40 (brd, 2H), 7.18 (s, 1H), 7.14 (s, 1H), 6.87 (brd, 8H), 4.51 (t, J=4.8 Hz, 2H), 4.25-4.19 (m, 4H), 4.16-4.09 (m, 6H), 3.97 (brd, 2H), 3.86-3.84 (m, 8H), 3.76-3.68 (m, 8H), 3.39 (brd, 2H), 2.32 (s, 6H), 2.16 (s, 6H), 2.03-1.93 (brd, 2H) (unit: ppm).

(2) TRO-A0015

Among the rotaxane compounds according to the present invention, a compound in which m=n=3 is referred to as "TRO-A0015". This TRO-A0015 was synthesized by a reaction shown by the following Chemical Formula 7.

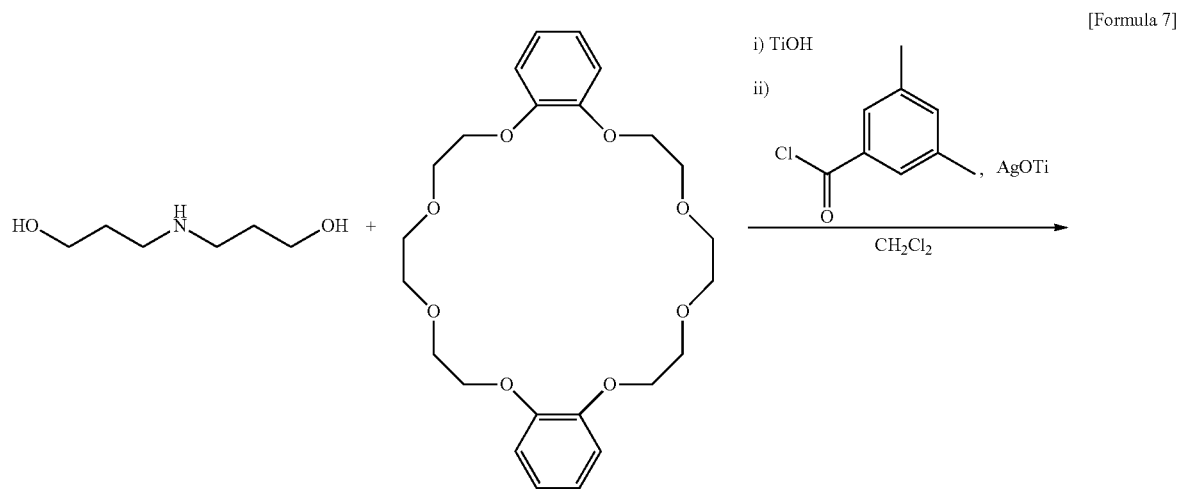

[Formula 7]

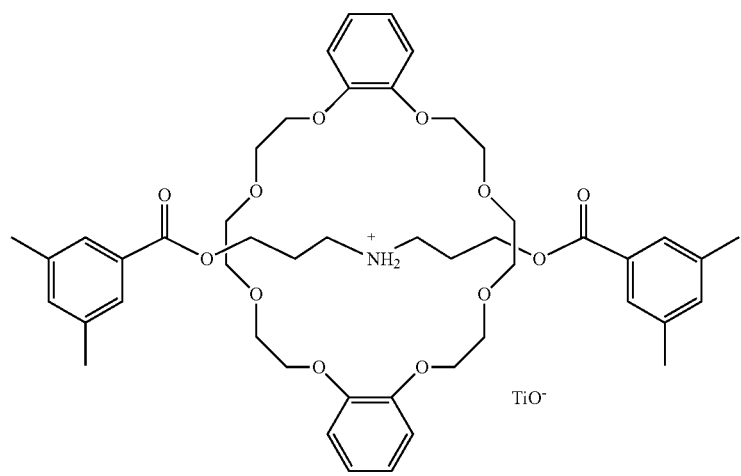

Specifically, 3,3'-azanediyldipropan-1-ol (200 mg, 1.50 mmol), dibenzo-24-crown-8-ether (808 mg, 1.80 mmol), and trifluoromethanesulfonic acid (133 mL, 1.50 mmol) were placed in a two-necked eggplant-shaped flask, followed by replacement with argon and then dissolution in $CH_2Cl_2$ (1 mL). The resulting solution was cooled to 0° C. and was stirred. Then, 3,5-dimethylbenzoyl chloride (608 mg, 3.61 mmol), having been replaced with argon and dissolved in $CH_2Cl_2$ (2 mL), was added thereto. Furthermore, after addition of silver trifluoromethanesulfonate (926 mg, 3.61 mmol), the temperature of the resulting mixture was gradually increased from 0° C. to room temperature, and the mixture was successively stirred at room temperature for 27 hours. After confirmation of TLC ($CHCl_3$/MeOH=10/1), saturated aqueous $Na_2CO_3$ was added to quench the reaction. Organic materials were extracted from the reaction mixture with $CHCl_3$, dried over $MgSO_4$, and subjected to filtration. The solvent was distilled away under reduced pressure. The obtained crude product was applied to silica gel column chromatography (eluent: $CHCl_3$/MeOH=1/0 to 10/1) and then to recycling HPLC (eluent: $CHCl_3$) for separation and purification to obtain a target compound.

The target compound was white-foamed solid, and the amount was 142 mg and the yield was 9%. The $^1H$ NMR spectrum (400 MHz, $CDCl_3$, 298 K) of the obtained target compound was as follows, and it was confirmed that the obtained compound was the compound on the right side of the above-mentioned Chemical Formula 7:

That is, δ 7.54 (s, 4H), 7.17 (s, 2H), 6.86 (brd, 8H), 4.18-4.17 (m, 8H), 4.12 (t, J=6.4 Hz, 4H), 3.88-3.87 (m, 8H), 3.73 (brd, 8H), 3.56-3.47 (m, 4H), 2.30 (s, 12H), 2.04-1.94 (m, 4H) (unit: ppm).

(3) TRO-A0010

Among the rotaxane compounds according to the present invention, a compound in which m=n=5 is referred to as "TRO-A0010". This TRO-A0010 shown by the following Chemical Formula 8 was synthesized by the following process.

That is, bis(1-pentanol)amine (190 mg, 0.65 mmol), dibenzo-24-crown-8-ether (350 mg, 0.78 mmol), and trifluoromethanesulfonic acid (58 mL, 0.65 mmol) were placed in a two-necked eggplant-shaped flask, followed by replacement with argon and then dissolution in $CH_2Cl_2$ (1.2 mL). The resulting solution was cooled to 0° C. and was stirred. After 12 hours, 3,5-dimethylbenzoic acid anhydride (367 mg, 1.30 mmol) was added thereto. Then, the temperature of the resulting mixture was gradually increased from 0° C. to room temperature, and the mixture was successively stirred at room temperature for 6 hours. After confirmation of TLC ($CHCl_3$/MeOH=10/1), saturated aqueous $Na_2CO_3$ was added to quench the reaction. Organic materials were extracted from the reaction mixture with $CHCl_3$, washed with 1 M HCl aqueous brine, dried over $MgSO_4$, and subjected to filtration. The solvent was distilled away under reduced pressure. The obtained crude product was applied to silica gel column chromatography (eluent: $CHCl_3$/MeOH=1/0 to 10/1) and then to recycling HPLC (eluent: $CHCl_3$) for separation and purification to obtain a target compound.

The target compound was white-foamed solid, and the amount was 388 mg and the yield was 57%. The $^1H$ NMR spectrum (400 MHz, $CDCl_3$, 298 K) of the obtained target compound was as follows, and it was confirmed that the obtained compound was the compound in the above-mentioned Chemical Formula 8:

That is: δ 7.59 (s, ArH, 4H), 7.18 (s, ArH, 2H), 6.89-6.83 (m, ArH, 8H), 4.14 (m, $CH_2$, 8H), 4.08 (t, J=6.4 Hz, $CH_2$, 4H), 3.86 (m, $CH_2$, 8H), 3.70 (m, $CH_2$, 8H), 3.25 (m, $CH_2$, 4H), 2.34 (s, dimethyl of end cap, $CH_3$, 12H), 1.54-1.44 (m, $CH_2$, 8H), 1.26-1.17 (m, $CH_2$, 4H) (unit: ppm).

(4) TRO-A0001

In addition, as a comparative control of each of the rotaxane compounds, a rotaxane compound "TRO-A0001" in which m=n=2 was used. This TRO-A0001 is the compound described in Patent Document 1 as described above and is represented by the following Chemical Formula 9.

[Formula 8]

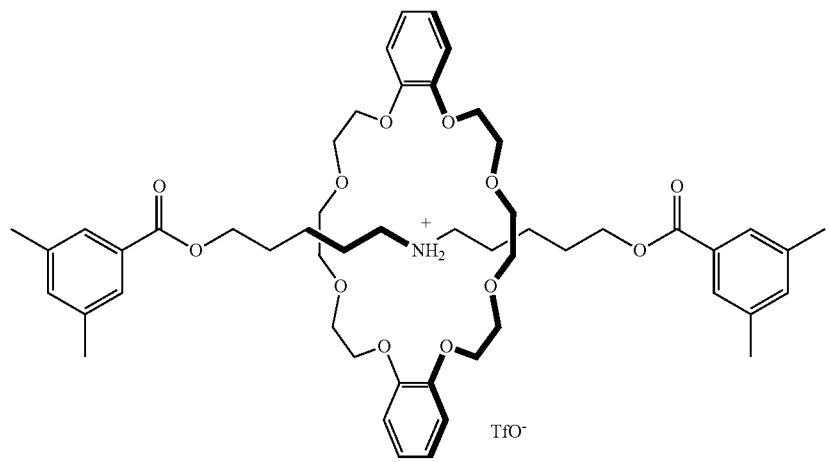

[Formula 9]

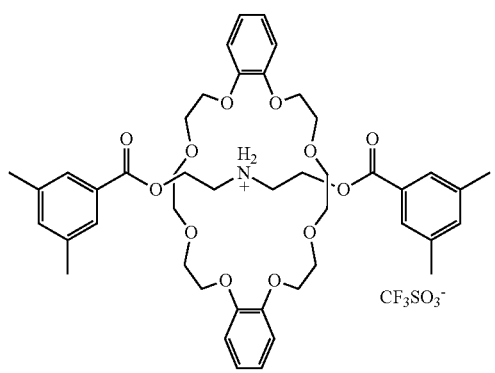

(I)

(5) Verification of Antitumor Activity (5-1) Experimental Conditions

As tumor cells, mouse colon tumor cell-derived cell line Colon-26, human glioblastoma-derived cell line T98G, and human malignant melanoma-derived cell line G361 were used. The tumor cells of each cell line were cultured in RPMI 1640 containing 10% FBS and 0.5% penicillin-streptomycin, as the base medium, in the presence of 5% $CO_2$, at 37° C., under humidity conditions. The tumor cells ($5.0 \times 10^4$) of each cell line having been cultured to a sufficiently confluent state were seeded in a 1.5 mL tube together with the medium. Each of the rotaxane compounds was dissolved in DMSO as a vehicle (solvent) and was added to the tube in a predetermined concentration so that the total amount is 1000 µL. Then, 100 µL of this was dispensed to each well of a 96-well microplate and was incubated in a $CO_2$ incubator for 24 hours. Subsequently, 10 µL of a viable-cell-counting reagent (Tetra Color ONE, a product of Seikagaku Corporation) was added to each well of the 96-well microplate, and a reaction was performed in the $CO_2$ incubator for 2 hours. The ultraviolet absorbance at 450 nm (control wavelength: 620 nm) was measured 72 hours after the reaction with a microplate reader. Note that the higher absorbance means the lager number of viable cells.

(5-2) Antitumor Activities of TRO-A0014 and TRO-A0015

The antitumor activities of TRO-A0014 and TRO-A0015 were verified using Colon-26 as tumor cells as in the method of (5-1) described above. The results are shown in FIG. 1. Note that in the drawing, "Vehicle" means the case of culturing the cells in the presence of only DMSO as a solvent and in the absence of the rotaxane compounds, and "Control" means the case of culturing the cells in the absence of the rotaxane compounds and DMSO.

As a result, in TRO-A0001 (m=n=2) as the comparative control, the cell growth-inhibiting effect was observed at a concentration 2.5 µM or more, but the effect at a concentration of 1.25 µM did not substantially differ from that of "Control" not to show the effect. On the other hand, in TRO-A0014 (m=2, n=3) and TRO-A0015 (m=n=3), the cell growth-inhibiting effect was obviously observed even at a concentration of 1.25 µM.

Therefore, it is obvious that the antitumor activities of TRO-A0014 (m=2, n=3) and TRO-A0015 (m=n=3) appear at lower concentration compared to that of TRO-A0001 (m=n=2).

(5-3) Antitumor Activity of TRO-A0010

Figure 2:
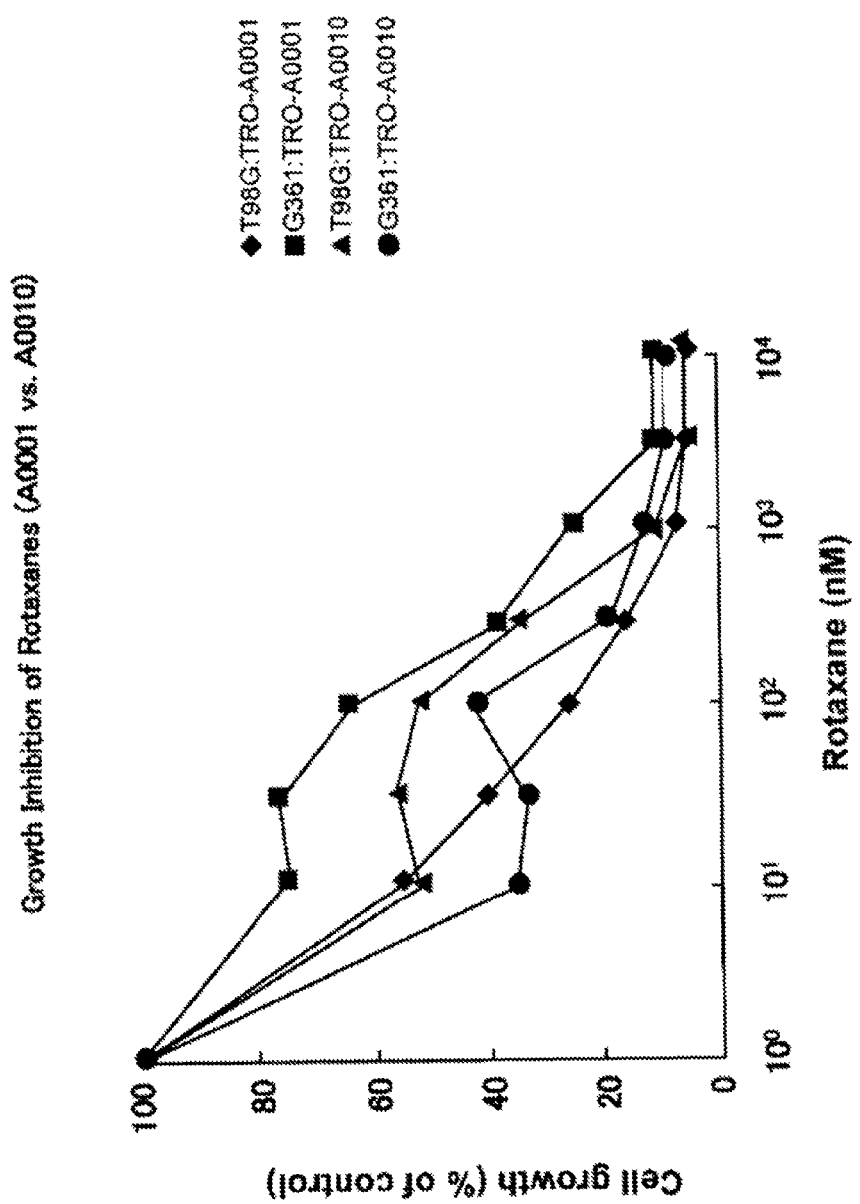
FIG. 2 A graph showing experimental results of antitumor activity of TRO-A0010.

The antitumor activity of TRO-A0010 was verified using T98G and G361 as tumor cells as in the above (5-1). The results are shown in FIG. 2.

As a result, in T98G, the antitumor activity of TRO-A0010 was similar to that of TRO-A0001. In addition, it was confirmed that in G361, the cell growth-inhibiting effect of TRO-A0010 was higher than that of TRO-A0001 at every rotaxane concentrations. Therefore, it was made clear that the antitumor activity of TRO-A0010 (m=n=5) was comparable to or, depending on the cell line, higher than that of TRO-A0001 (m=n=2).

INDUSTRIAL APPLICABILITY

The present invention can be used as an antitumor agent.

The invention claimed is:
1. A rotaxane compound, comprising:
a compound represented by the following Chemical Formula 1 as a basic structure

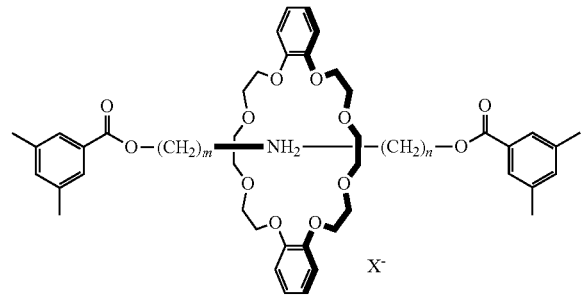

wherein $5 \geq m \geq 2$ and $5 \geq n \geq 3$ and X is an anionic molecule or an anionic atom.

2. A medicament, comprising the rotaxane compound according to claim 1 as an active ingredient.

3. The rotaxane compound according to claim 1, wherein m=2, n=3.

4. The rotaxane compound according to claim 1, wherein m=2, n=4.

5. The rotaxane compound according to claim 1, wherein m=2, n=5.

6. The rotaxane compound according to claim 1, wherein m=3, n=3.

7. The rotaxane compound according to claim 1, wherein m=3, n=4.

8. The rotaxane compound according to claim 1, wherein m=3, n=5.

9. The rotaxane compound according to claim 1, wherein m=4, n=4.

10. The rotaxane compound according to claim 1, wherein m=4, n=5.

11. The rotaxane compound according to claim 1, wherein m=5, n=5.

12. A method of inhibiting tumor cell growth in a subject, comprising:
administering a compound represented by the following Chemical Formula 1 as a basic structure to said subject,

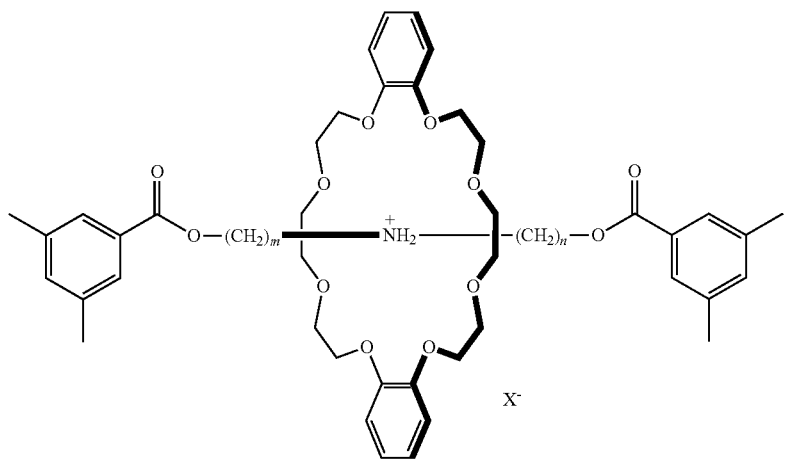
wherein $5 \geq m \geq 2$ and $5 \geq n \geq 3$ and X is an anionic molecule or an anionic atom, and wherein said tumor cell is a colon cancer cell, a glioblastoma cancer cell or a melanoma cancer cell.
\* \* \* \* \*